United States Patent
Miyamoto et al.

(10) Patent No.: US 8,491,467 B2
(45) Date of Patent: *Jul. 23, 2013

(54) ENDOSCOPE, DISTAL END CAP-EQUIPPED ENDOSCOPE AND ENDOSCOPE CLEANING SHEATH

(75) Inventors: Shinichi Miyamoto, Hachioji (JP); Akira Suzuki, Uenohara (JP)

(73) Assignee: Olympus Medical Systems Corp. (JP)

( * ) Notice: Subject to any disclaimer, the term of this patent is extended or adjusted under 35 U.S.C. 154(b) by 257 days.

This patent is subject to a terminal disclaimer.

(21) Appl. No.: 12/410,711

(22) Filed: Mar. 25, 2009

(65) Prior Publication Data

US 2009/0247830 A1  Oct. 1, 2009

(30) Foreign Application Priority Data

Mar. 31, 2008  (JP) ................................. 2008-091919

(51) Int. Cl.
*A61B 1/12* (2006.01)
(52) U.S. Cl.
USPC ........... 600/157; 121/129; 121/156; 121/158; 121/169
(58) Field of Classification Search
USPC ......................... 600/101–183; 239/86, 288.5
See application file for complete search history.

(56) References Cited

U.S. PATENT DOCUMENTS

| | | | | |
|---|---|---|---|---|
| 5,725,477 | A * | 3/1998 | Yasui et al. | 600/127 |
| 6,409,657 | B1 * | 6/2002 | Kawano | 600/157 |
| 2006/0161047 | A1 * | 7/2006 | Miyoshi | 600/157 |
| 2007/0260120 | A1 * | 11/2007 | Otawara | 600/129 |
| 2008/0188715 | A1 * | 8/2008 | Fujimoto | 600/157 |

FOREIGN PATENT DOCUMENTS

| | | |
|---|---|---|
| JP | 6-014870 | 1/1994 |
| JP | 7-136102 | 5/1995 |
| JP | 10-151108 | 6/1998 |
| JP | 11-188004 | 7/1999 |

* cited by examiner

*Primary Examiner* — Matthew J Kasztejna
*Assistant Examiner* — Kevin G Barry, III
(74) *Attorney, Agent, or Firm* — Ostrolenk Faber LLP

(57) ABSTRACT

An endoscope including, an insertion section, a distal end section body which constitutes a distal end section of the insertion section and has at least an observation window, a first flow path which is formed to supply a liquid to the distal end section body side and communicates with a first fluid source, a second flow path which is formed to supply a gas to the distal end section body side and communicates with a second fluid source, and a nozzle having a jet outlet which jets a mixture fluid, in which a fluid supplied from the first flow path and a fluid supplied from the second flow path are mixed, toward the observation window, wherein the observation window is disposed, relative to the jet outlet, on a side of one of the first flow path and the second flow path, which has a smaller fluid supply amount.

6 Claims, 10 Drawing Sheets

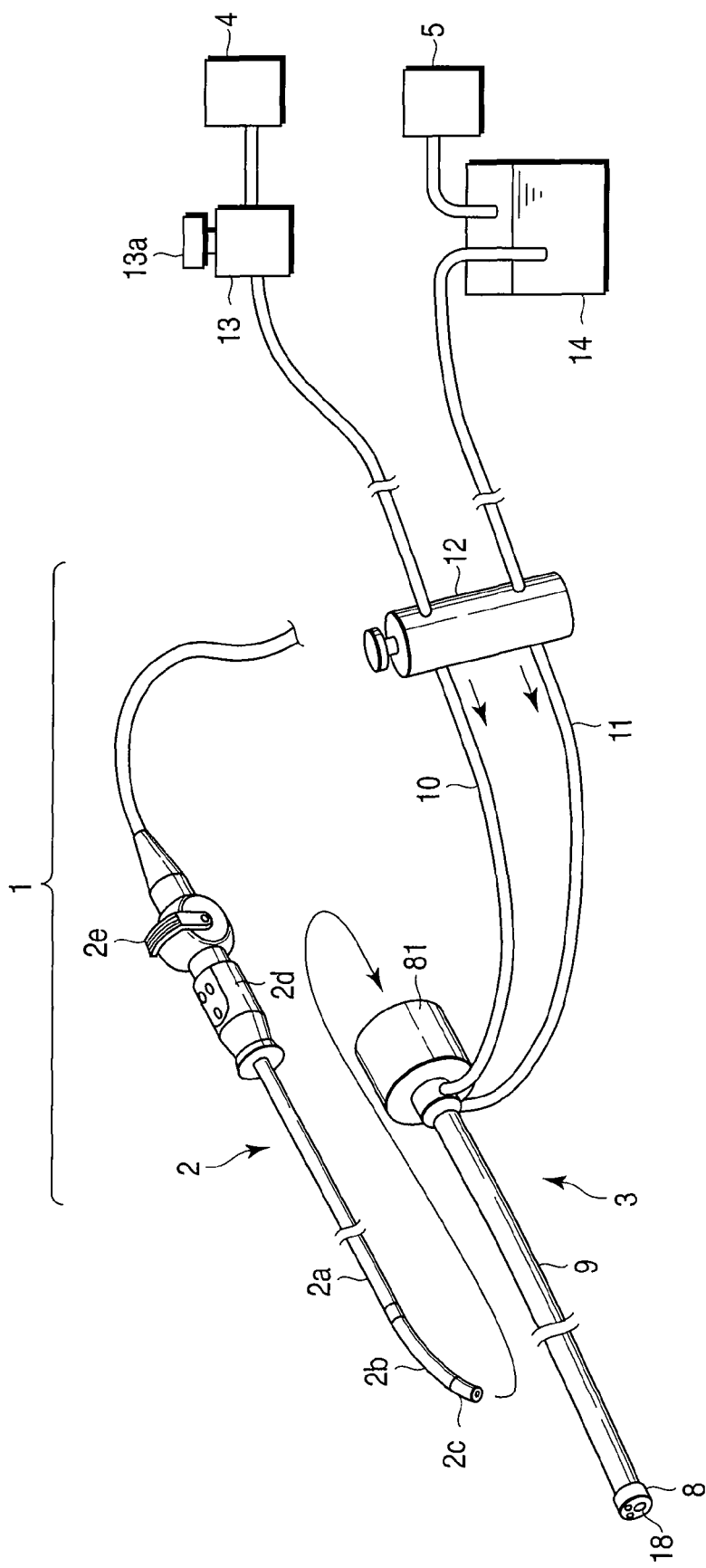
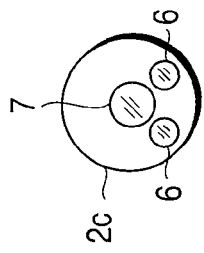
FIG. 1A
FIG. 1B

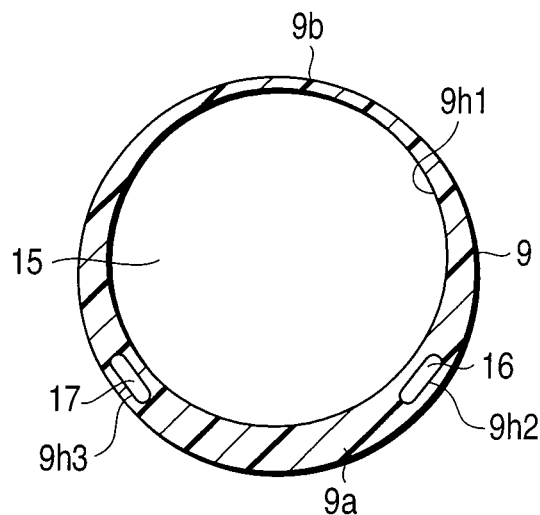
F I G. 2
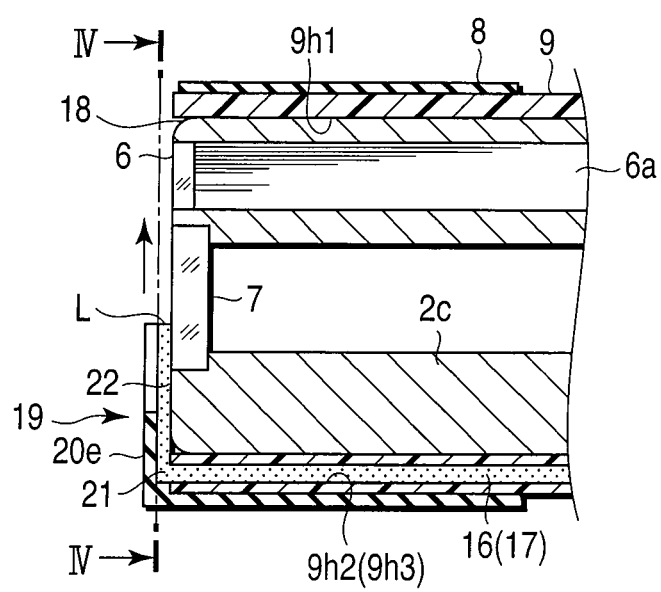
F I G. 3

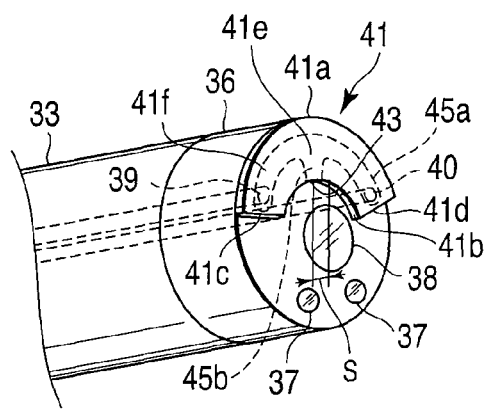
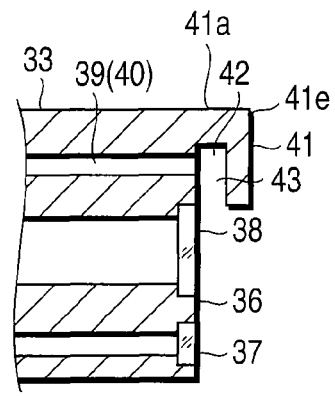
FIG. 7      FIG. 8
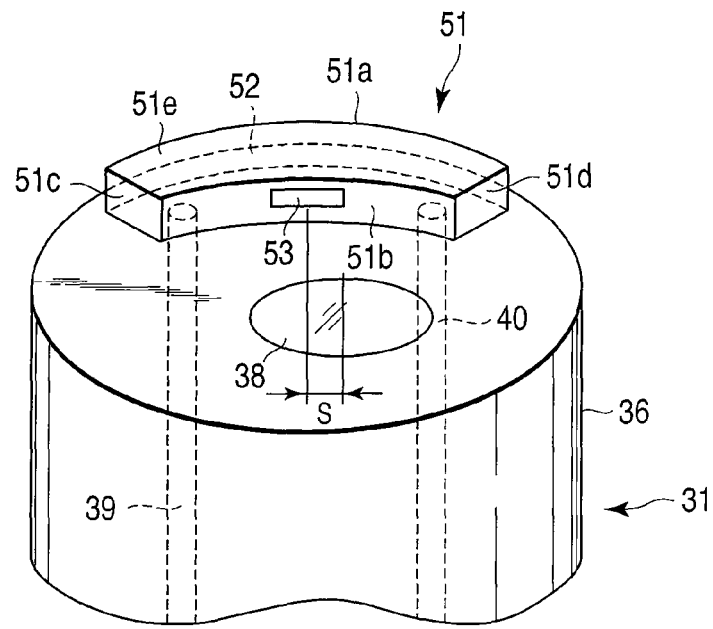
FIG. 10
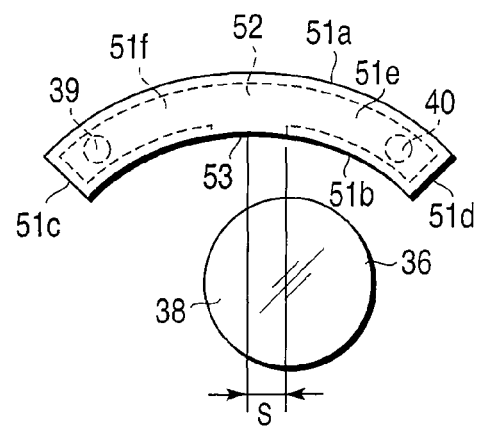
FIG. 11

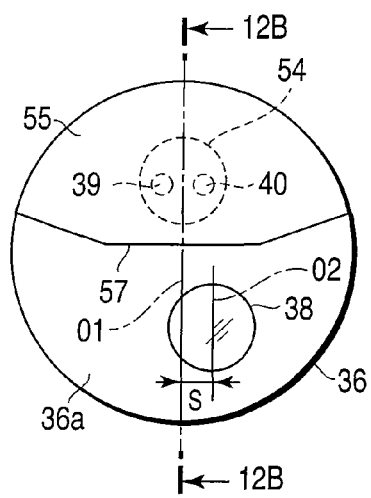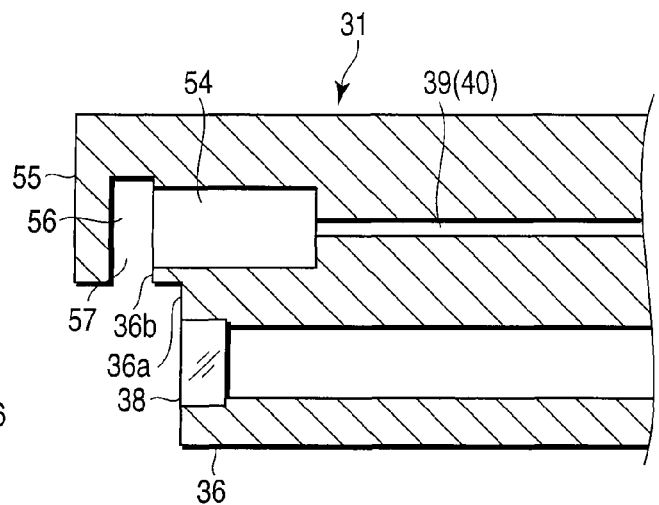
FIG. 12A  FIG. 12B
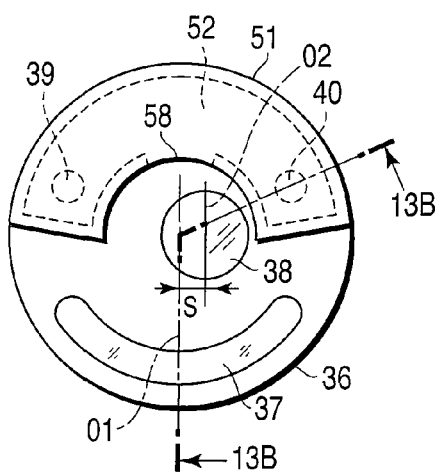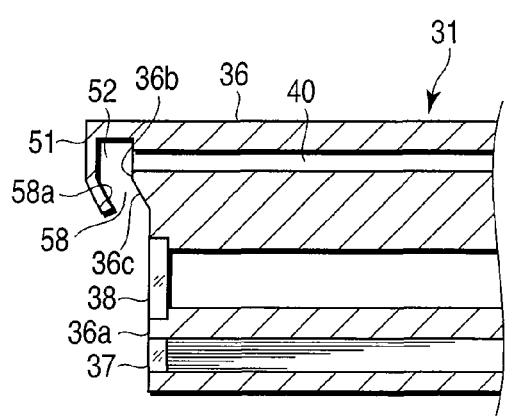
FIG. 13A  FIG. 13B

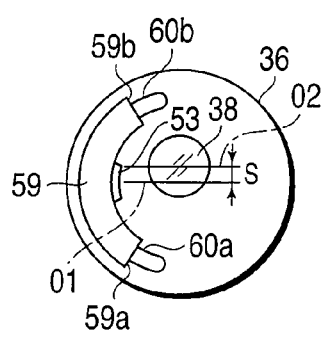 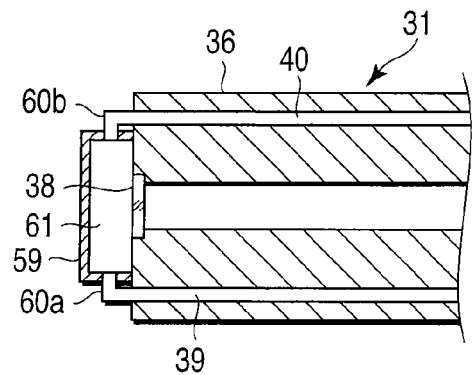
FIG. 14A        FIG. 14B
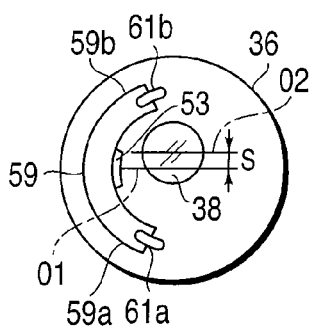 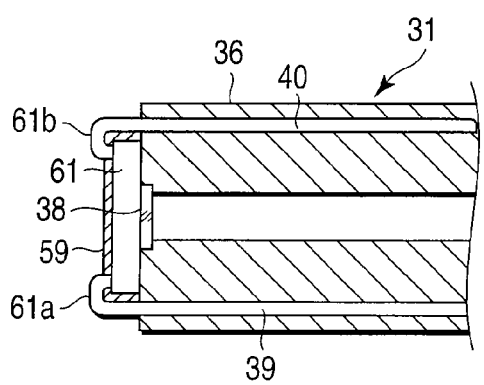
FIG. 15A        FIG. 15B
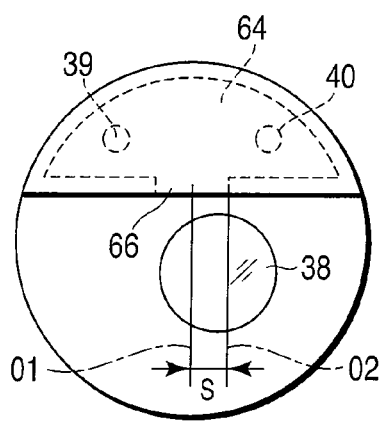 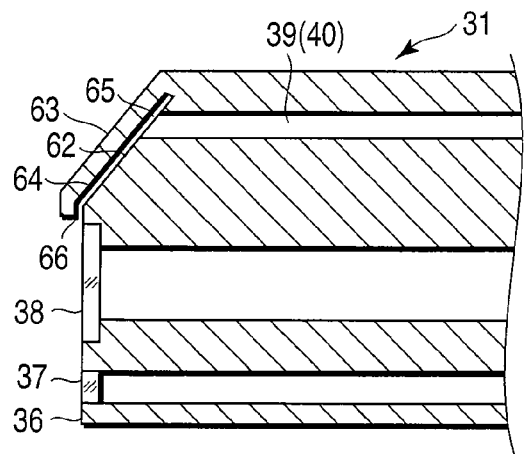
FIG. 16A        FIG. 16B

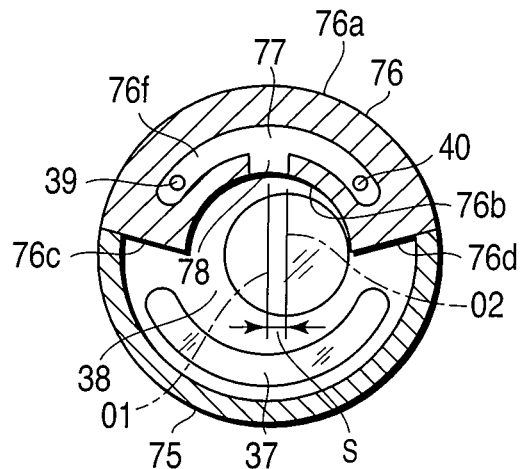
F I G. 20
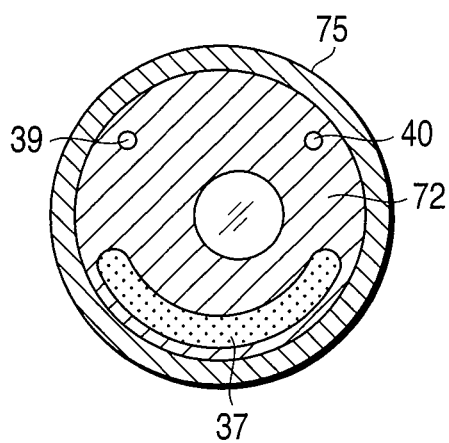
F I G. 21

ENDOSCOPE, DISTAL END CAP-EQUIPPED ENDOSCOPE AND ENDOSCOPE CLEANING SHEATH

CROSS-REFERENCE TO RELATED APPLICATIONS

This application is based upon and claims the benefit of priority from prior Japanese Patent Application No. 2008-091919, filed Mar. 31, 2008, the entire contents of which are incorporated herein by reference.

BACKGROUND OF THE INVENTION

1. Field of the Invention

The present invention relates to an endoscope including a fluid jet nozzle for cleaning, e.g. contamination adhering to an observation window which is provided on a distal end section body of the endoscope, a distal end cap-equipped endoscope, and an endoscope cleaning sheath.

2. Description of the Related Art

In a medical endoscope, an insertion section, which is inserted into a body cavity, is provided with an illumination window and an observation window at a distal end section body thereof. While emitting illumination light from the illumination window and illuminating the body cavity, observation is performed through the observation window. The distal end section body is provided with a fluid jet nozzle. In a case where blood, mucus or the like adheres to the illumination window or observation window and the field of vision is deteriorated, water and air are jetted from the fluid jet nozzle, thereby to clean the illumination window or observation window.

Jpn. Pat. Appln. KOKAI Publication No. H11-188004 (patent document 1) discloses the following structure. A distal end cap is detachably attached to a distal end section body of an insertion section of an endoscope. This distal end cap includes the air/water feed nozzle as mentioned above.

An air feed path and a water feed path are formed in the distal end section body. Distal end portions of a water feed tube and an air feed tube are connected, respectively, to the air feed path and the water feed path. A communication path, at which the air feed path and the water feed path are made confluent, is provided in the distal end section body. The air/water feed nozzle is connected to the communication path.

Proximal end portions of the water feed tube and air feed tube are connected to water feed means and air feed means on the proximal side of the insertion section. Water and air are supplied to the water feed tube and air feed tube from the water feed means and air feed means on the proximal side of the insertion section. In this structure, the water, which is fed from the water feed tube, and the air, which is fed from the air feed tube, are supplied to the air/water feed nozzle via the communication path in the distal end section body, and the water and air are jetted from the air/water feed nozzle to the observation window.

Jpn. Pat. Appln. KOKAI Publication No. H10-151108 (patent document 2), like patent document 1, discloses a structure wherein a water feed tube and an air feed tube are connected to a water feed path and an air feed path in a distal end section body of an endoscope, and the water feed tube and the air feed tube are made confluent in a communication path which is provided in the distal end section body. In addition, an air/water feed nozzle having a distal end portion with a reduced diameter is connected to the communication path. In this structure, water and air are jetted from the air/water feed nozzle to the observation window.

Jpn. Pat. Appln. KOKAI Publication No. H7-136102 (patent document 3) discloses the following structure. An air feed outlet and a water feed outlet, which open at a distal end face of a distal end potion body of an insertion section of an endoscope, are provided adjacent to each other. In the distal end section body, a nozzle is detachably attached in such a manner that the nozzle is opposed to the air feed outlet and water feed outlet. In this structure, the direction of jet of the air, which is fed from the air feed outlet, and the direction of jet of the water, which is fed from the water feed outlet, are varied by the nozzle, and the air and water are jetted toward the observation window.

Jpn. Pat. Appln. KOKAI Publication No. H6-14870 (patent document 4) discloses the following structure. An air feed path and a water feed path are provided in an insertion section of an endoscope. The air feed path and water feed path are made confluent in the insertion section, and made to communicate with an air/water feed nozzle. Further, air is intermittently blown into the water flowing in the water feed path, thus producing an air/water mixture fluid and enhancing the performance of cleaning.

BRIEF SUMMARY OF THE INVENTION

According to a first aspect of the present invention, an endoscope comprising: an insertion section which is inserted in a body cavity; a distal end section body which constitutes a distal end section of the insertion section and has at least an observation window; a first flow path which is formed to supply a liquid to the distal end section body side and communicates with a first fluid source; a second flow path which is formed to supply a gas to the distal end section body side and communicates with a second fluid source; and a nozzle having a jet outlet which jets a mixture fluid, in which a fluid supplied from the first flow path and a fluid supplied from the second flow path are mixed, toward the observation window, wherein the observation window is disposed, relative to the jet outlet, on a side of one of the first flow path and the second flow path, which has a smaller fluid supply amount.

According to another aspect of the present invention, an endoscope comprising: an insertion section which is inserted in a body cavity; a distal end section body which constitutes a distal end section of the insertion section and has at least an observation window; a first flow path which is formed to supply a liquid to the distal end section body side and communicates with a first fluid source; a second flow path which is formed to supply a gas to the distal end section body side and communicates with a second fluid source; and a nozzle having a jet outlet which jets a mixture fluid, in which a fluid supplied from the first flow path and a fluid supplied from the second flow path are mixed, toward the observation window, wherein the jet outlet is disposed, relative to the observation window, on a side of one of the first flow path and the second flow path, which has a greater fluid supply amount.

According to another aspect of the present invention, a distal end cap-equipped endoscope comprising: an insertion section which is inserted in a body cavity; a distal end section body which constitutes a distal end section of the insertion section and has at least an observation window; a first flow path which is formed to supply a liquid to the distal end section body side and communicates with a first fluid source; a second flow path which is formed to supply a gas to the distal end section body side and communicates with a second fluid source; a distal end cap which is detachably attached to the distal end section body; and a nozzle which is provided in the distal end cap and has a jet outlet which jets a mixture fluid, in which a fluid supplied from the first flow path and a fluid supplied from the second flow path are mixed, toward the observation window, wherein the observation window is disposed on the distal end section body, relative to the jet outlet, with an eccentricity on a side of one of the first flow path and the second flow path, which has a smaller fluid supply amount.

According to another aspect of the present invention, a distal end cap-equipped endoscope comprising: an insertion section which is inserted in a body cavity; a distal end section body which constitutes a distal end section of the insertion section and has at least an observation window; a first flow path which is formed to supply a liquid to the distal end section body side and communicates with a first fluid source; a second flow path which is formed to supply a gas to the distal end section body side and communicates with a second fluid source; a distal end cap which is detachably attached to the distal end section body; and a nozzle which is provided in the distal end cap and has a jet outlet which jets a mixture fluid, in which a fluid supplied from the first flow path and a fluid supplied from the second flow path are mixed, toward the observation window, wherein the jet outlet is disposed, relative to the observation window, with an eccentricity on a side of one of the first flow path and the second flow path, which has a greater fluid supply amount.

According to another aspect of the present invention, an endoscope cleaning sheath comprising: a cleaning sheath body which is fitted over an insertion section of an endoscope having at least an observation window at a distal end section body; a first flow path which is provided in the cleaning sheath body and communicates with a first fluid source; a second flow path which is provided in the cleaning sheath body and communicates with a second fluid source; and a nozzle which is provided in the cleaning sheath body and has a jet outlet which jets a mixture fluid, in which a fluid supplied from the first flow path and a fluid supplied from the second flow path are mixed, toward the observation window, wherein the observation window is disposed on the distal end section body, relative to the jet outlet, with an eccentricity on a side of one of the first flow path and the second flow path, which has a smaller fluid supply amount.

According to another aspect of the present invention, an endoscope cleaning sheath comprising: a cleaning sheath body which is fitted over an insertion section of an endoscope having at least an observation window at a distal end section body; a first flow path which is provided in the cleaning sheath body and communicates with a first fluid source; a second flow path which is provided in the cleaning sheath body and communicates with a second fluid source; and a nozzle which is provided in the cleaning sheath body and has a jet outlet which jets a mixture fluid, in which a fluid supplied from the first flow path and a fluid supplied from the second flow path are mixed, toward the observation window, wherein the jet outlet is disposed, relative to the observation window, with an eccentricity on a side of one of the first flow path and the second flow path, which has a greater fluid supply amount.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1A is a perspective view showing the entire structure of an endoscope and an endoscope cleaning sheath according to a first embodiment of the present invention;

FIG. 1B is a front view of a distal end section body of the endoscope;

FIG. 2 is a transverse cross-sectional view of a sheath body in the first embodiment;

FIG. 3 is a longitudinal cross-sectional side view of the distal end section of the endoscope in the first embodiment;

FIG. 7 is a perspective view of a distal end portion of an endoscope according to the third embodiment;

FIG. 8 is a longitudinal cross-sectional side view of the distal end portion of the endoscope according to the third embodiment;

FIG. 10 is a perspective view of a nozzle of a distal end portion according to a fourth embodiment of the present invention;

FIG. 11 is a front view of the nozzle of the distal end section body in the fourth embodiment;

FIG. 12A is a front view of a distal end section body according to a fifth embodiment of the present invention;

FIG. 12B is a cross-sectional view taken along line 12B-12B in FIG. 12A;

FIG. 13A is a front view of a distal end section body according to a sixth embodiment of the present invention;

FIG. 13B is a cross-sectional view taken along line 13B-13B in FIG. 13A;

FIG. 14A is a front view of a distal end section body according to a seventh embodiment of the present invention;

FIG. 14B is a longitudinal cross-sectional side view of the distal end section body;

FIG. 15A is a front view of a distal end section body according to an eighth embodiment of the present invention;

FIG. 15B is a longitudinal cross-sectional side view of the distal end section body;

FIG. 16A is a front view of a distal end section body according to a ninth embodiment of the present invention;

FIG. 16B is a longitudinal cross-sectional side view of the distal end section body;

FIG. 20 shows the eleventh embodiment and is a cross-sectional view taken along line 20-20 in FIG. 19; and FIG. 21 shows the eleventh embodiment and is a cross-sectional view taken along line 21-21 in FIG. 19.

DETAILED DESCRIPTION OF THE INVENTION

Figure 4:
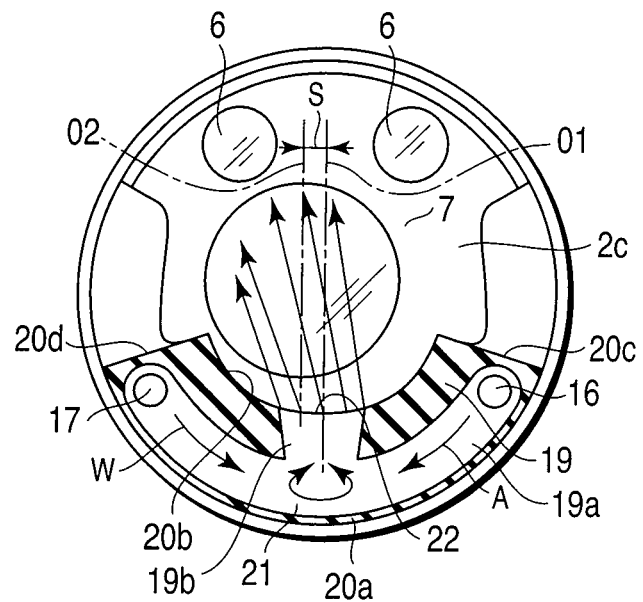
FIG. 4 is a cross-sectional view taken along line IV-IV in FIG. 3 in the first embodiment.

Embodiments of the present invention will now be described with reference to the accompanying drawings. FIG. 1A to FIG. 4 show a first embodiment of the present invention. FIG. 1A is a perspective view showing the entire structure of an endoscope apparatus, and FIG. 1B is a front view of a distal end section body of an endoscope.

As shown in FIG. 1A, an endoscope apparatus 1 comprises an endoscope 2, an endoscope cleaning sheath 3, a gas feed pump 4 functioning as a gas feed device, and a liquid feed pump 5 functioning as a liquid feed device. The endoscope 2 is, for example, a rigid endoscope having a bending section 2b in an insertion section 2a thereof. A distal end portion of the insertion section 2a is provided with a distal end section body 2c. A proximal end portion of the insertion section 2a is provided with an operation section 2d. The operation section 2d is provided with a bending operation lever 2e for bending the bending section 2b in an up-and-down direction or in a right-and-left direction.

The endoscope cleaning sheath 3 is fitted over the insertion section 2a of the endoscope 2. Thereby, the endoscope cleaning sheath 3, as one piece with the insertion section 2a, is inserted into a body cavity. As shown in FIG. 1B, a distal end face of the distal end section body 2c is provided with two illumination windows 6 and one observation window 7. The illumination widows 6 constitute parts of an illumination optical system. The observation window 7 constitutes a part of an observation optical system.

The illumination window 6 is connected to a light source device (not shown) via a light guide fiber 6a (see FIG. 3). The observation window 7 is provided with an image pickup device including an image pickup element, such as a CCD, which photoelectrically converts an optical image, which is captured through the observation optical system, to an electric signal. A signal cable extends from the image pickup device. This signal cable is connected to a camera control unit (not shown). Thus, reflective light from a subject, which is illuminated with illumination light that is emitted from the illumination window 6, is received as an optical image via the observation window 7. The optical image, after converted to the electric signal by the image pickup element, is transmitted to the camera control unit. The camera control unit generates a video signal on the basis of the electric signal, and outputs the video signal to, for example, a liquid crystal display which is a display device, thus displaying an endoscopic image on the screen of the liquid crystal display.

The endoscope cleaning sheath 3 is formed as an elongated cylindrical member. The insertion section 2a of the endoscope 2 is detachably inserted into the endoscope cleaning sheath 3. Thereby, the endoscope cleaning sheath 3 is disposed in a manner to cover the entirety of the insertion section 2a of the endoscope 2.

The endoscope cleaning sheath 3 is mainly composed of a distal end cover 8 which is a cylindrical body, and a tube body 9 which is composed of a multi-lumen tube. The distal end cover 8 is fitted on a distal end portion of the tube body 9 in a state in which the distal end cover 8 covers the outer peripheral surface of the distal end portion of the tube body 9. The proximal end side of the tube body 9 is provided with an operation section coupling unit 81 which has a greater diameter than the tube body 9. One end of a gas supply tube 10 and one end of a liquid supply tube 11 are coupled to the operation section coupling unit 81.

The other end of the gas supply tube 10 is connected to the gas feed pump 4 via an opening/closing valve 12 and a pressure adjusting valve 13, which are provided at positions along the gas supply tube 10. The other end of the liquid supply tube 11 is connected to the liquid feed pump 5 via the opening/closing valve 12 and a liquid feed tank 14, which are provided at positions along the liquid supply tube 11.

The tube body 9, which is composed of the multi-lumen tube, is formed of a flexible material such as silicone, urethane or TEFLON (PTFE) (trademark), or a rigid material such as polyamide, polyethylene, polypropylene or polycarbonate.

As shown in FIG. 2, the tube body 9 has an eccentric hole 9h1, the center axis of which is eccentric to the outer peripheral surface of the tube body 9. Thereby, the peripheral wall of the tube body 9, which defines the eccentric hole 9h1, includes a large thickness portion 9a and a small thickness portion 9b. The eccentric hole 9h1 of the tube body 9 is a through-hole having openings at a distal end face and a proximal end face of the tube body 9. The eccentric hole 9h1 is used as an endoscope hole 15 in which the insertion section 2a of the endoscope 2 is inserted. The large thickness portion 9a of the tube body 9 includes two through-holes 9h2 and 9h3, which penetrate the large thickness portion 9a in the axial direction of the tube body 9. One through-hole 9h2 is used as a gas feed path 16 serving as a first flow path for supplying a gas such as air. The other through-hole 9h3 is used as a liquid feed path 17 serving as a second flow path for supplying a liquid such as water or a cleaning solution. The proximal end side of the gas feed path 16 communicates with the gas supply tube 10, and the proximal end side of the liquid feed path 17 communicates with the liquid supply tube 11.

The distal end cover 8 of the endoscope cleaning sheath 3 is a circular cylindrical member which covers the distal end portion of the tube body 9. As shown in FIG. 3, the distal end cover 8 is provided with an opening portion 18 at a part thereof that is opposed to the front surface of the distal end section body 2c of the endoscope 2.

A nozzle 19, which is bent inward in a substantially L shape, is integrally provided in a front end portion of the distal end cover 8. As shown in FIG. 4, the nozzle 19 is formed in an arcuate shape along the outer peripheral portion of the distal end section body 2c. The nozzle 19 is disposed at a position facing the front surface of the large thickness portion 9a of the tube body 9.

An arcuate communication groove 19a for communication between the gas feed path 16 and the liquid feed path 17 is formed in the nozzle 19. In the nozzle 19, an outer peripheral wall 20a of the communication groove 19a is closed in a sealed state. A nozzle opening portion 19b is formed at a substantially central position in the inner peripheral wall 20b of the communication groove 19a. Thereby, the communication groove 19a of the nozzle 19 has a space portion which is surrounded by the outer peripheral wall 20a extending along the outer peripheral portion of the distal end section body 2c, the inner peripheral wall 20b surrounding a part of the outer periphery of the observation window 7, right and left end walls (right end wall 20c, left end wall 20d) in FIG. 4, and an arcuate front wall 20e (see FIG. 3).

Further, the gas feed path 16 is open on the right end wall 20c side in the space portion of the communication groove 19a of the nozzle 19. On the opposite side of the communication groove 19a, that is, on the left end wall 20d side, the liquid feed path 17 is open. Accordingly, the gas feed path 16 and the liquid feed path 17 communicate via the communication groove 19a. In addition, in the nozzle 19, the nozzle opening portion 19b of the inner peripheral wall 20b communicates with the communication groove 19a. The nozzle opening portion 19b is open toward the front end side of the distal end section body 2c of the endoscope 2.

A confluent portion 21 is provided in an intermediate part in the longitudinal direction of the communication groove 19a of the nozzle 19. The confluent portion 21 is a part which combines the gas (arrow A in FIG. 4) that is supplied from the gas feed path 16 and the liquid (arrow W in FIG. 4) that is supplied from the liquid feed path 17, causes the gas and liquid to temporarily stay there, and mixes the gas and liquid.

The diameter of the flow path of the confluent portion 21 is set to be greater than the diameter of the flow path of each of the gas feed path 16 and liquid feed path 17. Thereby, the gas that is supplied from the gas feed path 16 and the liquid that is supplied from the liquid feed path 17 collide with each other and are made turbulent, and the gas and liquid are efficiently mixed.

The nozzle opening portion 19b of the inner peripheral wall 20b is disposed at a position facing the confluent portion 21 of the communication groove 19a. The nozzle opening portion 19b is formed of a jet outlet 22 which is made of a rectangular elongated hole that is elongated in the longitudinal direction of the nozzle 19. Thereby, the gas/liquid mixture fluid, which is made confluent and mixed in the confluent portion 21, is jetted toward the observation window 7 from the jet outlet 22 of the inner peripheral wall 20b of the nozzle 19.

The jet outlet 22 and the observation window 7 are disposed in such a positional relationship that the center line O2 of the observation window 7 is biased by an eccentricity amount (S) to the opening end side of the liquid feed path 17, relative to the center line O1 of the jet outlet 22. In general, there is a difference in specific gravity between a liquid and a gas (the specific gravity of the gas is less than that of the liquid (gas<liquid)). In consideration of the difference in specific gravity between the liquid and gas, the supply amount of the liquid, which is supplied from the liquid feed path 17, is set to be less than the supply amount of the gas which is supplied from the gas feed path 16. Thereby, the gas and liquid are efficiently mixed, and a forceful jet is produced.

The observation window 7 is disposed with a bias to the liquid feed path 17 side, on which the fluid supply amount is small. By this structure, an atomized gas/liquid mixture fluid, which is jetted from the jet outlet 22, is sprayed on the observation window 7, while being properly adjusted so as to reach the entire surface of the observation window 7, as indicated by arrows in FIG. 4.

The gas that is supplied from the gas feed path 16 and the liquid that is supplied from the liquid feed path 17 are mixed in the confluent portion 21, and an atomized gas/liquid mixture fluid is produced. This atomized gas/liquid mixture fluid is jetted toward the observation window 7 from the jet outlet 22. At this time, the confluent portion 21 of the nozzle 19 is provided at the distal end surface of the distal end section body 2c on the same plane that continuously extends to the observation window 7. Thereby, contamination (mucus, blood, etc.) adhering to the observation window 7 is blown off and cleaned by the atomized gas/liquid mixture fluid that is jetted from the jet outlet 22. In the present embodiment, the illumination windows 6 are disposed on the downstream side of the observation window 7, relative to the flow of the gas/liquid mixture fluid that is jetted from the nozzle 19. In this case, since the illumination windows 6 are also provided on the plane that is continuous with the confluent portion 21 of the nozzle 19, contamination adhering to the illumination windows 6 can be blown off and cleaned by the flow of the gas/liquid mixture fluid that is jetted from the nozzle 19.

Next, the operation of the first embodiment is described. If the endoscope cleaning sheath 3 is fitted over the insertion section 2a of the endoscope 2, the entirety of the insertion section 2a is covered with the tube body 9, and the distal end section body 2c of the endoscope 2 is covered with the distal end cover 8. At this time, the jet outlet 22, which is provided in the nozzle 19 of the distal end cover 8, is set in the state in which the jet outlet 22 is so disposed as to be directed to the observation window 7 and illumination windows 6 which are provided on the distal end section body 2c.

In the state in which the endoscope cleaning sheath 3 is fitted over the endoscope 2, the insertion section 2a of the endoscope 2, as one piece with the endoscope cleaning sheath 3, is inserted into a body cavity of a patient. In this state, the inside of the body cavity is observed by the endoscope 2, and a diseased part is treated, where necessary. At this time, if contamination adheres to the observation window 7 and the field of vision of the endoscope 2 is deteriorated, or if contamination adheres to the illumination window 6 and the illuminance lowers, the observation window 7 can be cleaned remotely.

Specifically, at the time of cleaning, the gas feed pump 4 is driven to feed gas and simultaneously the liquid feed pump 5 is driven to feed liquid. If the gas is fed from the gas feed pump 4, the gas is supplied to the gas feed path 16 via the gas supply tube 10. If the liquid is fed from the liquid feed pump 5, the liquid is supplied to the liquid feed path 17 via the liquid supply tube 11. Further, the gas in the gas feed path 16 and the liquid in the liquid feed path 17 are supplied into the nozzle 19. At this time, the gas supplied from the gas feed path 16 and the liquid supplied from the liquid feed path 17 collide and made turbulent in the confluent portion 21. As a result, the liquid and gas are mixed in the confluent portion 21, and an atomized gas/liquid mixture fluid is produced. The gas/liquid mixture fluid is jetted from the jet outlet 22 toward the observation window 7.

At this time, the confluent portion 21 of the nozzle 19 is provided on the same plane that is continuous with the observation window 7 and illumination windows 6 which are provided on the distal end section body 2c. Further, the observation window 7 is disposed with the eccentricity amount (S) to the liquid feed path 17 side, on which the fluid supply amount is small. In this state, the atomized gas/liquid mixture fluid, which is jetted from the jet outlet 22, is sprayed on the observation window 7, while being properly adjusted so as to reach the entire surface of the observation window 7. Therefore, the atomized gas/liquid mixture fluid, which is mixed in the confluent portion 21, is jetted from the jet outlet 22 toward the surface of the observation window 7, and the contamination adhering to the observation window 7 and illumination windows 6 can efficiently be blown off and cleaned. Moreover, since the jetted fluid is the atomized gas/liquid mixture fluid, no drops of water remain on the surfaces of the observation window 7 and illumination windows 6, and the field of vision, as well as the illuminance, can instantaneously be secured.

Since the illumination windows 6 are disposed on the downstream side of the observation window 7, relative to the flow of the gas/liquid mixture fluid that is jetted from the nozzle 19, the illumination windows 6 and the observation window 7 can be cleaned at the same time by the flow of the gas/liquid mixture fluid that is jetted from the nozzle 19.

Figure 5:
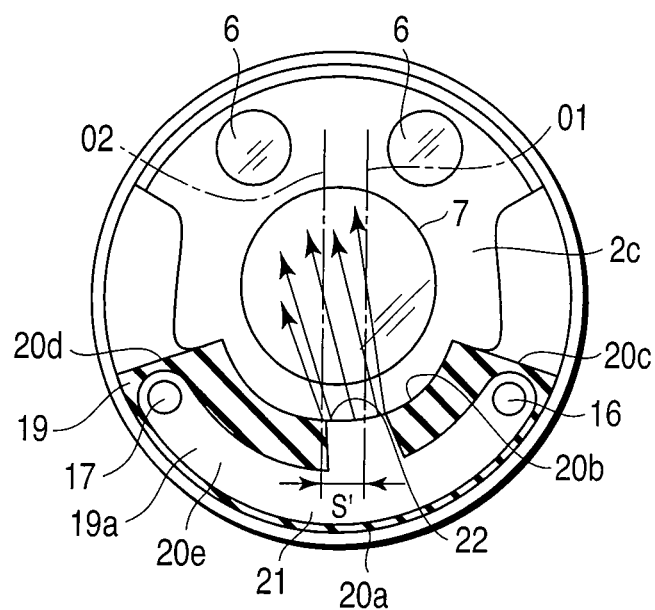
FIG. 5 shows a second embodiment of the present invention, and is a cross-sectional view showing the structure at a position corresponding to line IV-IV cross section in FIG. 3.

FIG. 5 shows a second embodiment of the present invention. In FIG. 5, the structural parts, which are common to those in the first embodiment (see FIG. 1A to FIG. 4), are denoted by like reference numerals, and a description thereof is omitted.

In the present embodiment, the positional relationship between the jet outlet 22 and the observation window 7 is altered in the following manner. Specifically, the center line O2 of the observation window 7 is disposed at a substantially central position of the front surface of the distal end section body 2c of the endoscope 2. The center line O1 of the jet outlet 22 is biased by an eccentricity amount (S') to the opening end side of the gas feed path 16, relative to the center line O2 of the observation window 7. Specifically, in consideration of the difference in specific gravity between the liquid and gas (i.e. the gas<the liquid), the supply amount of the liquid, which is supplied from the liquid feed path 17, is set to be less than the supply amount of the gas which is supplied from the gas feed path 16, thereby to efficiently mix the gas and liquid and to produce a forceful jet. The jet outlet 22 is disposed with a bias to the gas feed path 16 side, on which the fluid supply amount is large. By this structure, the atomized gas/liquid mixture fluid, which is jetted from the jet outlet 22, is sprayed on the observation window 7, while being properly adjusted so as to reach the entire surface of the observation window 7.

The above-described embodiments are directed to the case in which the cleaning tube is fitted over the rigid endoscope. Needless to say, however, the invention is applicable to the case in which the cleaning tube is fitted over a flexible endoscope.

Figure 6:
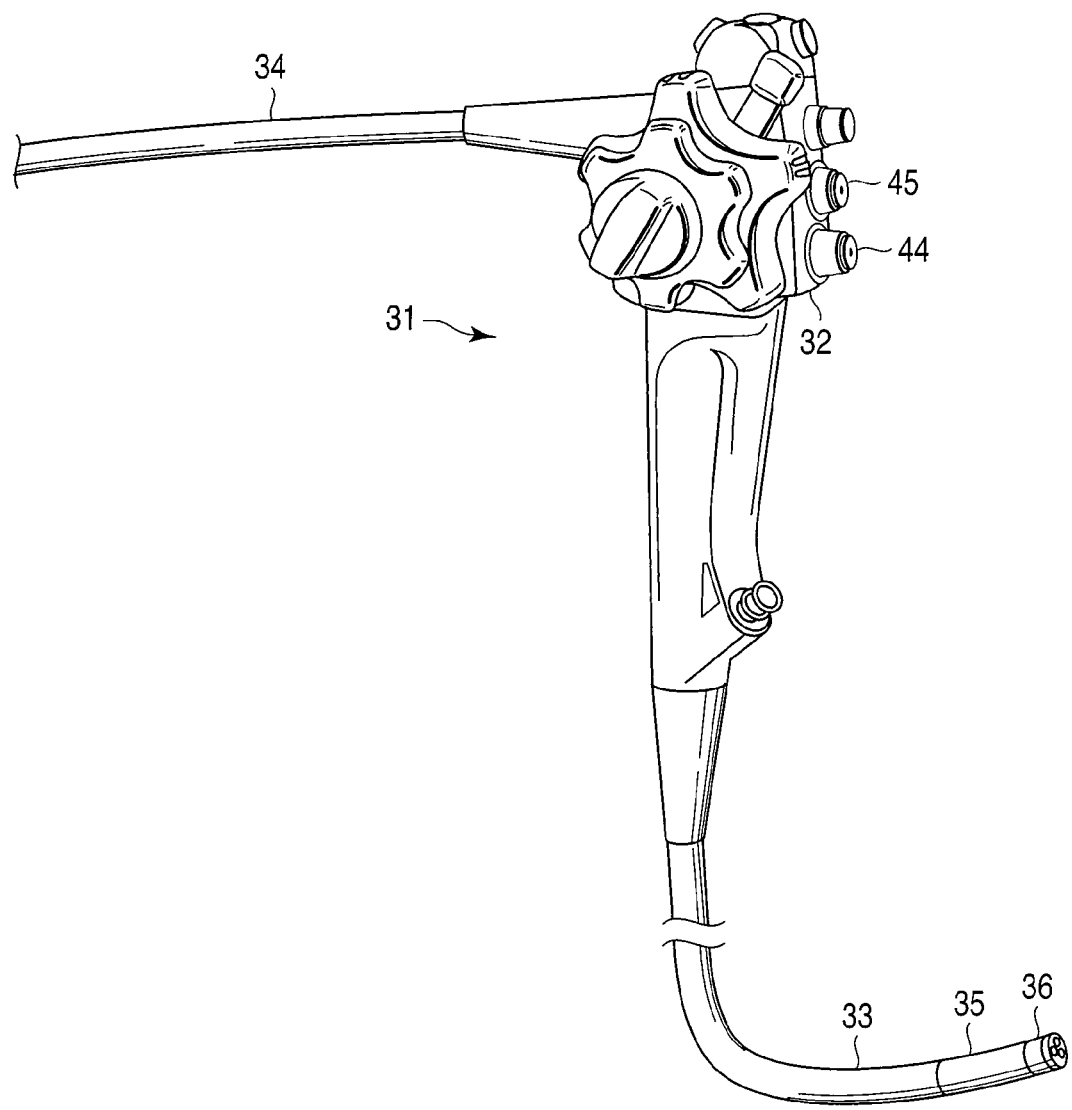
FIG. 6 is a perspective view of a flexible endoscope according to a third embodiment of the present invention.

FIG. 6 to FIG. 8 show a third embodiment of the present invention. In this embodiment, a flexible endoscope 31 shown in FIG. 6 is integrally equipped with a cleaning function. FIG. 6 is a perspective view showing the entirety of the flexible endoscope 31.

As shown in FIG. 6, in the flexible endoscope 31, a flexible insertion section 33 and a universal cord 34 are coupled to an operation section 32. A distal end section body 36 is provided on the insertion section 33 via a bending section 35. As shown in FIG. 7 and FIG. 8, the distal end section body 36 is provided with illumination windows 37 which constitute parts of an illumination optical system, and an observation window 38 which constitutes a part of an observation optical system. The illumination window 37 is connected to a light source device (not shown) via a light guide fiber. The observation optical system is provided with an image pickup device (not shown) including an image pickup element, such as a CCD, which photoelectrically converts an optical image, which is captured through the observation window 38, to an electric signal.

The insertion section 33 is provided with a gas feed path 39 for supplying a gas such as air, and a liquid feed path 40 for supplying a liquid such as water or a cleaning solution. Like the first embodiment, the gas feed path 39 and liquid feed path 40 communicate with the gas feed pump 4 and liquid feed pump 5 through the insertion section 33, operation section 32 and universal cord 34.

As shown in FIG. 8, an arcuate nozzle 41 is integrally provided at a front end portion of the distal end section body 36 of the endoscope 31 along the outer peripheral part of this front end portion.

An arcuate communication groove 45a for communication between the gas feed path 39 and the liquid feed path 40 is formed in the nozzle 41. In the nozzle 41, an outer peripheral wall 41a of the communication groove 45a is closed in a sealed state. A nozzle opening portion 45b is formed at a substantially central position in the inner peripheral wall 41b of the communication groove 45a. Thereby, the communication groove 45a of the nozzle 41 has a space portion 41f which is surrounded by the outer peripheral wall 41a extending along the outer peripheral portion of the distal end section body 36, the inner peripheral wall 41b surrounding a part of the outer periphery of the observation window 38, left and right end walls (left end wall 41c, right end wall 41d) in FIG. 7, and an arcuate front wall 41e. The space portion 41f is curved in an arcuate shape according to the curvature of the outer peripheral wall 41a and inner peripheral wall 41b. A taper portion, which is tapered toward the distal end opening, is formed in the nozzle opening portion 45b at the intermediate part of the space portion 41f. Thereby, a substantially T-shaped conduit is formed of the communication groove 45a and nozzle opening portion 45b of the nozzle 41.

Further, the gas feed path 39 is open on the left end wall 41c side in the space portion 41f of the nozzle 41. On the right end wall 41d side, the liquid feed path 40 is open. Accordingly, the gas feed path 39 and the liquid feed path 40 are open to the front end side of the distal end section body 36, and are opposed to the inner surface of the front wall 41e of the nozzle 41.

An intermediate part in the longitudinal direction of the nozzle 41 is provided with a confluent portion 42 which combines and mixes the gas that is supplied from the gas feed path 39 and the liquid that is supplied from the liquid feed path 40. Further, the nozzle opening portion 45b of the inner peripheral wall 41b of the nozzle 41, which is opposed to the confluent portion 42, is provided with a jet outlet 43 of the nozzle 41. The jet outlet 43 is configured to jet the gas/liquid mixture fluid, which is made confluent and mixed in the confluent portion 21, toward the observation window 7.

The confluent portion 42 of the nozzle 41, which has the above-described structure, is provided on the same plane that is continuous with the observation window 38 provided on the distal end section body 36. The gas supplied from the gas feed path 39 and the liquid supplied from the liquid feed path 40 collide in the confluent portion 42. Thereby, the liquid and gas are made turbulent and mixed into an atomized gas/liquid mixture fluid is produced. The gas/liquid mixture fluid is jetted from the jet outlet 43 toward the observation window 38. Thus, contamination adhering to the observation window 38 is blown off and cleaned by the atomized gas/liquid mixture fluid that is jetted from the jet outlet 43.

Further, the operation section 32 is provided with a gas/liquid feed button 44 and a suction button 45. The gas/liquid feed button 44 controls the flow amount of the gas supplied from the gas feed path 39 and the flow amount of the liquid supplied from liquid feed path 40, and controls the gas/liquid mixture fluid that is jetted in an atomized state from the jet outlet 43 of the nozzle 41. Like the first embodiment, the nozzle 41, observation window 38 and illumination windows 37 may successively be arranged on the same plane, so that the observation window 38 and illumination window 37 may be cleaned by the gas/liquid mixture fluid that is jetted from the nozzle 41 in the atomized state.

Next, the operation of the third embodiment is described. In the endoscope 31 of this embodiment, the nozzle 41 is integrally provided on the distal end section body 36 of the insertion section 33. The jet outlet 43 of the nozzle 41 is disposed on the same plane toward the observation window 38 and illumination windows 37. The insertion section 33 of the endoscope 31 is inserted into a body cavity of a patient, and the inside of the body cavity is observed and a diseased part is treated, where necessary. At this time, if contamination adheres to the observation window 38 and the field of vision is deteriorated, the observation window 38 can be cleaned remotely by the operation described below.

Specifically, the gas feed pump 4 is driven to feed gas and simultaneously the liquid feed pump 5 is driven to feed liquid. If the gas is fed from the gas feed pump 4, the gas is supplied to the gas feed path 39. Similarly, if the liquid is fed from the liquid feed pump 5, the liquid is supplied to the liquid feed path 40. Thus, the gas in the gas feed path 39 and the liquid in the liquid feed path 40 are supplied to the communication groove 45a in the nozzle 41. The gas supplied from the gas feed path 39 and the liquid supplied from the liquid feed path 40 are mixed in the confluent portion 42, and an atomized gas/liquid mixture fluid is produced and jetted from the jet outlet 43 toward the observation window 38.

At this time, since the confluent portion 42 of the nozzle 41 is provided on the same plane that is continuous with the observation window 38 which is provided on the distal end section body 36, the atomized gas/liquid mixture fluid, which is mixed in the confluent portion 42, is jetted toward the observation window 38, and the contamination adhering to the observation window 38 can efficiently be blown off and cleaned. Moreover, since the jetted fluid is the atomized gas/liquid mixture fluid and particles of water immediately evaporate, no drops of water remain on the surface of the observation window 38, and the field of vision, as well as the illuminance, can instantaneously be secured.

In the case where the force of the atomized gas/liquid mixture fluid, which is jetted from the jet outlet 43, is to be increased, the gas/liquid feed button 44 that is provided on the operation section 32 is controlled to increase the pressure of the gas. Thereby, the pressure of the gas that is supplied from the gas feed path 39 can be increased, and the gas/liquid mixture ratio can arbitrarily be controlled.

FIG. 9A to FIG. 9H show different modifications of the nozzle 41 in the third embodiment. Each of FIG. 9A to FIG. 9H is a schematic front view of the front end section body 36.

Figure 9A:
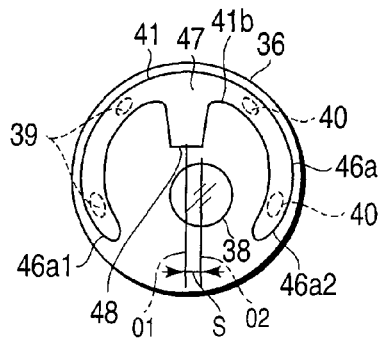
FIG. 9A is a schematic front view of a nozzle according to a first modification of the third embodiment.

FIG. 9A shows a nozzle 41 according to a first modification of the third embodiment. The nozzle 41 shown in FIG. 9A is provided with a substantially C-shaped arcuate portion 46a having a curvature according to the outer peripheral part of the distal end section body 36. Extension portions 46a1 and 46a2 at both ends of the arcuate portion 46a are made to extend from the center line position of the front end portion of the distal end section body 36 of the endoscope 31 up to 90° or more to both sides, respectively.

In the inside of the nozzle 41, a confluent portion 47 is provided at an intermediate part of the arcuate portion 46a. Further, a jet outlet 48, which projects toward the observation window 38, is provided in an inner peripheral wall 41b of the nozzle 41 at the intermediate part of the arcuate portion 46a.

In the arcuate portion 46a, two gas feed paths 39 are open on the left side and two liquid feed paths 40 are open on the right side in such a manner that the two gas feed paths 39 and the two liquid feed paths 40 are symmetric with respect to the confluent portion 47 as a boundary. The gas supplied from the two gas feed paths 39 and the liquid supplied from the two liquid feed paths 40 collide in the confluent portion 47. Thereby, the gas and liquid are made turbulent and mixed into an atomized gas/liquid mixture fluid, and the atomized gas/liquid mixture fluid is jetted from the jet outlet 48 toward the observation window 38.

The jet outlet 48 and the observation window 38 are disposed in such a positional relationship that the center line O2 of the observation window 38 is biased by an eccentricity amount (S) to the opening end side of the liquid feed paths 40, relative to the center line O1 of the jet outlet 48.

Figure 9B:
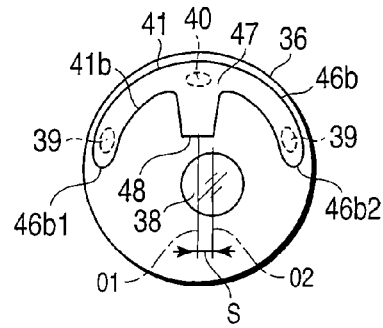
FIG. 9B is a schematic front view of a nozzle according to a second modification of the third embodiment.

FIG. 9B shows a nozzle 41 according to a second modification of the third embodiment. The nozzle 41 shown in FIG. 9B is provided with an arcuate conduit 46b having a curvature according to the outer peripheral part of the distal end section body 36. The length of the conduit 46b is less than the length of the arcuate portion 46a of the first modification. Specifically, extension portions 46b1 and 46b2 at both ends of the conduit 46b are made to extend from the center line position of the front end portion of the distal end section body 36 of the endoscope 31 to 90° or less to both sides, respectively.

A confluent portion 47 is provided at an intermediate part of the conduit 46b. Further, a jet outlet 48, which projects toward the observation window 38, is provided in an inner peripheral wall 41b of the nozzle 41 at the intermediate part of the conduit 46b.

In the confluent portion 47, one liquid feed path 40 is open. Two gas feed paths 39 are open symmetrically in the extension portions 46b1 and 46b2 at both ends of the conduit 46b. The liquid supplied from the one liquid feed path 40 and the gas supplied from the two gas feed paths 39 collide in the confluent portion 47. Thereby, the gas and liquid are made turbulent and mixed into an atomized gas/liquid mixture fluid, and the atomized gas/liquid mixture fluid is jetted from the jet outlet 48 toward the observation window 38.

The jet outlet 48 and the observation window 38 are disposed in such a positional relationship that the center line O2 of the observation window 38 is biased by an eccentricity amount (S) to the extension portion 46b2 at one end, relative to the center line O1 of the jet outlet 48.

Figure 9C:
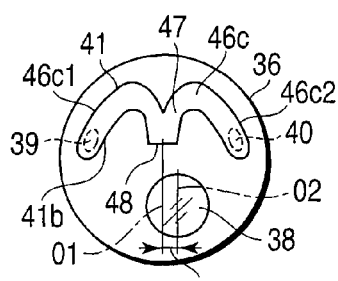
FIG. 9C is a schematic front view of a nozzle according to a third modification of the third embodiment.

FIG. 9C shows a nozzle 41 according to a third modification of the third embodiment. The nozzle 41 shown in FIG. 9C is provided with a substantially M-shaped conduit 46c at the front end portion of the distal end section body 36 of the endoscope 31. This conduit 46c includes left and right conduits (left conduit 46c1 and right conduit 46c2), each of which is bent in a substantially V shape with an acute angle, on both sides of the center line position of the front end portion of the front end section body 36 of the endoscope 31.

A confluent portion 47 is provided at a coupling part between the left conduit 46c1 and right conduit 46c2. Further, a jet outlet 48, which projects toward the observation window 38, is provided in an inner peripheral wall 41b of the nozzle 41 at the coupling part between the left conduit 46c1 and right conduit 46c2. A gas feed path 39 is open in the left conduit 46c1, and a liquid feed path 40 is open in the right conduit 46c2. The liquid supplied from the liquid feed path 40 of the right conduit 46c2 and the gas supplied from the gas feed path 39 of the left conduit 46c1 collide in the confluent portion 47. Thereby, the gas and liquid are made turbulent and mixed into an atomized gas/liquid mixture fluid, and the atomized gas/liquid mixture fluid is jetted from the jet outlet 48 toward the observation window 38.

The jet outlet 48 and the observation window 38 are disposed in such a positional relationship that the center line O2 of the observation window 38 is biased by an eccentricity amount (S) to the right conduit 46c2 side, relative to the center line O1 of the jet outlet 48.

Figure 9D:
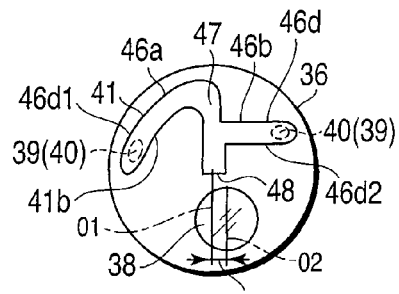
FIG. 9D is a schematic front view of a nozzle according to a fourth modification of the third embodiment.

FIG. 9D shows a nozzle 41 according to a fourth modification of the third embodiment. The nozzle 41 shown in FIG. 9D includes a conduit 46d at a front end portion of the distal end section body 36 of the endoscope 31. The conduit 46d is composed of an inverted-V-shaped portion 46d1 and a horizontal portion 46d2 communicating with one end portion of the inverted-V-shaped portion 46d1.

The inverted-V-shaped portion 46d1 is formed in the state in which the inverted-V-shaped portion 46d1 is curved along the outer peripheral part of the distal end section body 36. A confluent portion 47 is provided at a bent part of the inverted-V-shaped portion 46a. Further, a jet outlet 48, which projects toward the observation window 38, is provided in an inner peripheral wall 41b of the nozzle 41 at a coupling part between the inverted-V-shaped portion 46d1 and the horizontal portion 46d2. A gas feed path 39 (or a liquid feed path 40) is open on the left side of the conduit 46, and a liquid feed path 40 (or a gas feed path 39) is open on the right side. The liquid supplied from the liquid feed path 40 of the horizontal portion 46d2 and the gas supplied from the gas feed path 39 of the inverted-V-shaped portion 46d1 collide in the confluent portion 47. Thereby, the gas and liquid are made turbulent and mixed into an atomized gas/liquid mixture fluid, and the atomized gas/liquid mixture fluid is jetted from the jet outlet 48 toward the observation window 38.

The jet outlet 48 and the observation window 38 are disposed in such a positional relationship that the center line O2 of the observation window 38 is biased by an eccentricity amount (S) to the horizontal portion 46d2 side, relative to the center line O1 of the jet outlet 48.

Figure 9E:
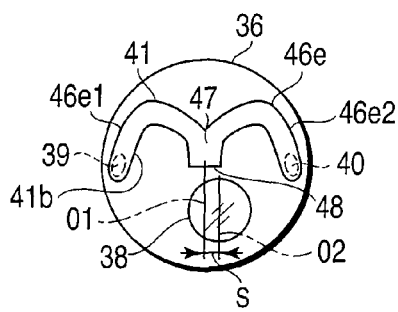
FIG. 9E is a schematic front view of a nozzle according to a fifth modification of the third embodiment.

FIG. 9E shows a nozzle 41 according to a fifth modification of the third embodiment. The nozzle 41 shown in FIG. 9E is provided with a substantially M-shaped conduit 46e at the front end portion of the distal end section body 36 of the endoscope 31. This conduit 46e includes left and right conduits (left conduit 46e1 and right conduit 46e2), each of which is bent in a substantially U shape with an obtuse angle, on both sides of the center line position of the front end portion of the front end section body 36 of the endoscope 31.

A confluent portion 47 is provided at a coupling part between the left conduit 46e1 and right conduit 46e2. Further, a jet outlet 48, which projects toward the observation window 38, is provided in an inner peripheral wall 41b of the nozzle 41 at the coupling part between the left conduit 46e1 and right conduit 46e2. A gas feed path 39 is open in the left conduit 46e1, and a liquid feed path 40 is open in the right conduit 46e2. The liquid supplied from the liquid feed path 40 of the right conduit 46e2 and the gas supplied from the gas feed path 39 of the left conduit 46e1 collide in the confluent portion 47. Thereby, the gas and liquid are made turbulent and mixed into an atomized gas/liquid mixture fluid, and the atomized gas/liquid mixture fluid is jetted from the jet outlet 48 toward the observation window 38.

The jet outlet 48 and the observation window 38 are disposed in such a positional relationship that the center line O2 of the observation window 38 is biased by an eccentricity amount (S) to the right conduit 46e2 side, relative to the center line O1 of the jet outlet 48.

Figure 9F:
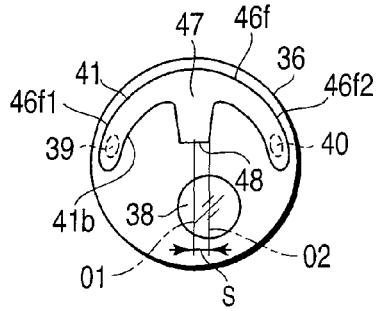
FIG. 9F is a schematic front view of a nozzle according to a sixth modification of the third embodiment.

FIG. 9F shows a nozzle 41 according to a sixth modification of the third embodiment. The nozzle 41 shown in FIG. 9F is provided with an arcuate conduit 46f having a curvature according to the outer peripheral part of the distal end section body 36. The length of the conduit 46f is less than the length of the arcuate portion 46a of the first modification. Specifically, extension portions 46f1 and 46f2 at both ends of the conduit 46f are made to extend from the center line position of the front end portion of the distal end section body 36 of the endoscope 31 to 90° or less to both sides, respectively.

A confluent portion 47 is provided at an intermediate part of the conduit 46f. Further, a jet outlet 48, which projects toward the observation window 38, is provided in an inner peripheral wall 41b of the nozzle 41 at the intermediate part of the conduit 46f.

A gas feed path 39 is open in the left-side extension portion 46f1 of the conduit 46f. A liquid feed path 40 is open in the right-side extension portion 46f2 of the conduit 46f. The liquid supplied from the liquid feed path 40 of the right-side extension portion 46f2 and the gas supplied from the gas feed path 39 of the left-side extension portion 46f1 collide in the confluent portion 47. Thereby, the gas and liquid are made turbulent and mixed into an atomized gas/liquid mixture fluid, and the atomized gas/liquid mixture fluid is jetted from the jet outlet 48 toward the observation window 38.

The jet outlet 48 and the observation window 38 are disposed in such a positional relationship that the center line O2 of the observation window 38 is biased by an eccentricity amount (S) to the right-side extension portion 46f2, relative to the center line O1 of the jet outlet 48.

Figure 9G:
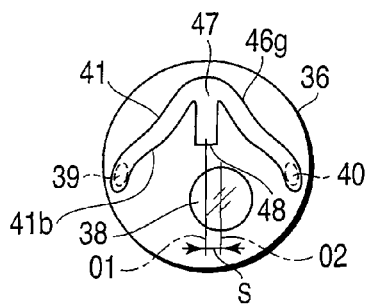
FIG. 9G is a schematic front view of a nozzle according to a seventh modification of the third embodiment.

FIG. 9G shows a nozzle 41 according to a seventh modification of the third embodiment. The nozzle 41 shown in FIG. 9G is provided with a substantially angular conduit 46g. A confluent portion 47 is provided at an intermediate part of the conduit 46g. Further, a jet outlet 48, which projects toward the observation window 38, is provided in an inner peripheral wall 41b of the nozzle 41 at the intermediate part of the conduit 46g. A gas feed path 39 is open on the left side of the conduit 46g, and a liquid feed path 40 is open on the right side of the conduit 46g. The liquid supplied from the right-side liquid feed path 40 of the conduit 46g and the gas supplied from the left-side gas feed path 39 of the conduit 46g collide in the confluent portion 47. Thereby, the gas and liquid are made turbulent and mixed into an atomized gas/liquid mixture fluid, and the atomized gas/liquid mixture fluid is jetted from the jet outlet 48 toward the observation window 38.

The jet outlet 48 and the observation window 38 are disposed in such a positional relationship that the center line O2 of the observation window 38 is biased by an eccentricity amount (S) to the right-side liquid feed conduit 40 side, relative to the center line O1 of the jet outlet 48.

Figure 9H:
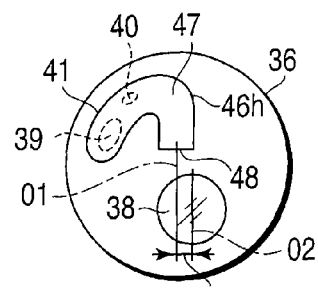
FIG. 9H is a schematic front view of a nozzle according to an eighth modification of the third embodiment.

FIG. 9H shows a nozzle 41 according to an eighth modification of the third embodiment. The nozzle 41 shown in FIG. 9H includes an inverted-V-shaped conduit 46h at a front end portion of the distal end section body 36 of the endoscope 31. A confluent portion 47 is provided at a bent part of the conduit 46h. Further, a jet outlet 48, which is open toward a side portion of the observation window 38 from the confluent portion 47, is provided. A large-diameter gas feed path 39 is open on a left-side end portion (on the upstream side) of the conduit 46h. A small-diameter liquid feed path 40 is open on the downstream side of the gas feed path 39. The gas supplied from the left-side gas feed path 39 of the conduit 46h and the liquid supplied from the liquid feed path 40 collide in the confluent portion 47. Thereby, the gas and liquid are made turbulent and mixed into an atomized gas/liquid mixture fluid, and the atomized gas/liquid mixture fluid is jetted from the jet outlet 48 toward the observation window 38.

The jet outlet 48 and the observation window 38 are disposed in such a positional relationship that the center line O2 of the observation window 38 is biased by an eccentricity amount (S) to the right side, relative to the center line O1 of the jet outlet 48.

According to each of the modifications having the above-described structures, the following advantageous effects can be obtained. Specifically, the confluent portion 47 of the nozzle 41 is provided on the same plane as the observation window 38 that is provided on the distal end section body 36. Therefore, the atomized gas/liquid mixture fluid, which is mixed in the confluent portion 47, is jetted toward the observation window 38, and the contamination adhering to the observation window 38 can efficiently be blown off and cleaned. Moreover, since the jetted fluid is the atomized gas/liquid mixture fluid, no drops of water remain on the surface of the observation window 38, and the field of vision can instantaneously be secured.

FIG. 10 and FIG. 11 show a fourth embodiment of the invention. The structural parts common to those in the third embodiment (see FIG. 6 to FIG. 8) are denoted by like reference numerals, and a description thereof is omitted.

An arcuate nozzle 51 is integrally provided at a front end portion of the distal end section body 36 of the endoscope 31 along the outer peripheral part of this front end portion. Specifically, the nozzle 51 includes a space portion (communication groove) 51*f* which is surrounded by an outer peripheral wall 51*a* extending along the outer peripheral portion of the distal end section body 36, an inner peripheral wall 51*b* surrounding a part of the outer periphery of the observation window 38, left and right end walls (left end wall 51*c*, right end wall 51*d*) in FIG. 10, and an arcuate front wall 51*e*. The space portion 51*f* is curved in an arcuate shape according to the curvature of the outer peripheral wall 51*a* and inner peripheral wall 51*b*. Further, the gas feed path 39 is open on the left end wall 51*c* side in the space portion 51*f* of the nozzle 51. On the opposite right end wall 51*d* side, the liquid feed path 40 is open. Accordingly, the gas feed path 39 and the liquid feed path 40 are open to the front end side of the distal end section body 36 of the endoscope 31, and are opposed to the inner surface of the front wall 51*e* of the nozzle 51.

An intermediate part in the longitudinal direction of the nozzle 51 is provided with a confluent portion 52 which combines and mixes the gas that is supplied from the gas feed path 39 and the liquid that is supplied from the liquid feed path 40. The flow path diameter of the confluent portion 52 is set to be greater than the flow path diameter of each of the gas feed path 39 and liquid feed path 40. Thereby, the gas and liquid collide in the confluent portion 52, and the gas and liquid are efficiently mixed. Further, a jet outlet 53, which is formed of a laterally elongated rectangular hole, is provided in the inner peripheral wall 51*b* of the nozzle 51, which is opposed to the confluent portion 52. The jet outlet 53 is configured to jet the gas/liquid mixture fluid, which is made confluent and mixed in the confluent portion 52, toward the observation window 38. The jet outlet 53 and the observation window 38 are disposed in such a positional relationship that the center line O2 of the observation window 38 is biased by an eccentricity amount (S) to the opening end side of the liquid feed path 40, relative to the center line O1 of the jet outlet 53.

With the above-described structure, the following advantageous effects can be obtained. Specifically, the confluent portion 52 of the nozzle 51 is provided on the same plane as the observation window 38 that is provided on the distal end section body 36. The gas supplied from the air feed path 39 and the liquid supplied from the liquid feed path 40 are mixed in the confluent portion 52 into an atomized gas/liquid mixture fluid. The atomized gas/liquid mixture fluid is jetted from the jet outlet 53 toward the observation window 38. Thereby, the contamination adhering to the observation window 38 can be blown off and cleaned by the gas/liquid mixture fluid that is jetted from the jet outlet 53.

FIG. 12A and FIG. 12B show a fifth embodiment of the invention. The structural parts common to those in the third and fourth embodiments (see FIG. 6 to FIG. 8, FIG. 10 and FIG. 11) are denoted by like reference numerals, and a description thereof is omitted.

As shown in FIG. 12A, an observation window 38 is provided at a front end portion of the distal end section body 36 of the endoscope 31. As shown in FIG. 12B, a projection portion 36*b*, which projects forward from a plane 36*a* in which the observation window 38 is provided, is provided adjacent to the observation window 38. This projection portion 36*b* is provided with a confluent portion 54, which is formed of a cylindrical recess portion, in the axial direction of the distal end section body 36. A gas feed path 39 and a liquid feed path 40 are open at the bottom of the confluent portion 54.

The projection portion 36*b* of the distal end section body 36 is integrally provided with a front end wall portion 55 which is opposed to the opening part of the confluent portion 54. A nozzle 56 is formed between the front end wall portion 55 and the opening part of the confluent portion 54. The nozzle 56 is provided with a jet outlet 57 which opens toward the observation window 38. As shown in FIG. 12A, the jet outlet 57 and the observation window 38 are disposed in such a positional relationship that the center line O2 of the observation window 38 is biased by an eccentricity amount (S) to the opening end side of the liquid feed path 40, relative to the center line O1 of the jet outlet 57.

With the above-described structure, the following advantageous effects can be obtained. Specifically, the confluent portion 54 of the nozzle 56 and the jet outlet 57 are parallel to the observation window 38 that is provided on the distal end section body 36, and are provided in a manner to project forward from the observation window 38. The gas supplied from the air feed path 39 and the liquid supplied from the liquid feed path 40 are mixed in the confluent portion 54 into an atomized gas/liquid mixture fluid. The gas/liquid mixture fluid collides with the inner surface of the front end wall portion 55 of the nozzle 56 and is further mixed in an atomized state. The atomized gas/liquid mixture fluid is jetted from the jet outlet 57 toward the observation window 38. Thereby, the contamination adhering to the observation window 38 can efficiently be blown off and cleaned by the gas/liquid mixture fluid that is jetted from the jet outlet 57.

FIG. 13A and FIG. 13B show a sixth embodiment of the invention. The structural parts common to those in the third to fifth embodiments (see FIG. 6 to FIG. 12B) are denoted by like reference numerals, and a description thereof is omitted.

As shown in FIG. 13A, an observation window 38 and an illumination window 37 are provided at a front end portion of the distal end section body 36 of the endoscope 31. As shown in FIG. 13B, a projection portion 36*b*, which projects forward from a plane 36*a* in which the observation window 38 is provided, is provided adjacent to the observation window 38. An inclined surface 36*c* is formed between the plane 36*a* and the projection portion 36*b*.

The projection portion 36*b* is provided with a nozzle 51 which is integral with the distal end section body 36. The nozzle 51 has basically the same structure as in the third embodiment. Specifically, the nozzle 51 is curved in an arcuate shape according to the curvature of the outer peripheral surface of the distal end section body 36. Further, a confluent portion 52 is provided at an intermediate part of the nozzle 51. The nozzle 51 is provided with a jet outlet 58 which is parallel to the inclined surface 36*c* and has a fluid guide surface 58*a* which projects toward the observation window 38. In addition, as shown in FIG. 13A, the jet outlet 58 and the observation window 38 are disposed in such a positional relationship that the center line O2 of the observation window 38 is biased by an eccentricity amount (S) to the opening end side of the liquid feed path 40, relative to the center line O1 of the jet outlet 58.

Besides, a gas feed path 39 and a liquid feed path 40 are open in the space portion of the nozzle 51. The gas feed path 39 and liquid feed path 40 are open toward the front end side of the distal end section body 36 of the endoscope 31, and are opposed to the inner surface of the nozzle 51.

With the above-described structure, the following advantageous effects can be obtained. Specifically, the confluent portion 52 of the nozzle 51 and the jet outlet 58 are parallel to the observation window 38 that is provided on the distal end section body 36, and are provided in a manner to project forward from the observation window 38. The gas supplied from the air feed path 39 and the liquid supplied from the liquid feed path 40 are mixed in the confluent portion 52 into a gas/liquid mixture fluid. The gas/liquid mixture fluid collides with the inner surface of the nozzle 51 and is further mixed in an atomized state. The atomized gas/liquid mixture fluid is jetted from the jet outlet 58 toward the observation window 38. Thereby, the contamination adhering to the observation window 38 can be blown off and cleaned by the gas/liquid mixture fluid that is jetted from the jet outlet 58.

FIG. 14A and FIG. 14B show a seventh embodiment of the invention. The structural parts common to those in the third to sixth embodiments (see FIG. 6 to FIG. 13B) are denoted by like reference numerals, and a description thereof is omitted.

A front end portion of the distal end section body 36 of the endoscope 31 includes an arcuate nozzle 59 which has the same structure as the nozzle 51 of the fourth embodiment (see FIG. 10 and FIG. 11) and is curved in an arcuate shape along the outer peripheral part of the distal end section body 36. The nozzle 59 includes a space portion which is surrounded by walls. As shown in FIG. 14B, an L-shaped conduit 60a, which is connected to the gas feed path 39, penetrates one end wall 59a (on the lower side in FIG. 14A) of the nozzle 59 and is open to the inside of the nozzle 59. Thereby, the nozzle 59 communicates with the L-shaped conduit 60a. An L-shaped conduit 60b, which is connected to the liquid feed path 40, penetrates the opposite-side end wall 59b (on the upper side in FIG. 14A) of the nozzle 59 and is open to the inside of the nozzle 59. Thereby, the nozzle 59 communicates with the L-shaped conduit 60b. Accordingly, the opening portions of the gas feed path 39 and the liquid feed path 40 are opposed to a confluent portion 61 at an intermediate part of the nozzle 59.

Further, a jet outlet 53, which is directed to the observation window 38, is provided at a central position of the inner peripheral wall of the nozzle 59. The jet outlet 53 is disposed at a position facing the confluent portion 61. Thus, the jet outlet 53 is configured to jet the gas/liquid mixture fluid, which is made confluent and mixed in the confluent portion 61, toward the observation window 38. The jet outlet 53 and the observation window 38 are disposed in such a positional relationship that the center line O2 of the observation window 38 is biased by an eccentricity amount (S) to the opening end side of the liquid feed path 40, relative to the center line O1 of the jet outlet 53.

With the above-described structure, the following advantageous effects can be obtained. Specifically, the confluent portion 61 of the nozzle 59 is provided on the same plane as the observation window 38 that is provided on the distal end section body 36. The gas supplied from the air feed path 39 and the liquid supplied from the liquid feed path 40 are mixed in the confluent portion 61 into an atomized gas/liquid mixture fluid. The atomized gas/liquid mixture fluid is jetted from the jet outlet 53 toward the observation window 38. Thereby, the contamination adhering to the observation window 38 can be blown off and cleaned by the gas/liquid mixture fluid that is jetted from the jet outlet 53.

FIG. 15A and FIG. 15B show an eighth embodiment of the invention. The structural parts common to those in the third to seventh embodiments (see FIG. 6 to FIG. 14B) are denoted by like reference numerals, and a description thereof is omitted.

A front end portion of the distal end section body 36 of the endoscope 31 includes an arcuate nozzle 59 which has the same structure as the nozzle 59 of the seventh embodiment (see FIG. 14A and FIG. 14B) and is curved in an arcuate shape along the outer peripheral part of the distal end section body 36. The nozzle 59 includes a space portion which is surrounded by walls. A U-shaped conduit 61a, which is connected to the gas feed path 39, penetrates a front surface portion of the nozzle 59 on one end wall 59a side (on the lower side in FIG. 15A) of the nozzle 59 and is open to the inside of the nozzle 59. Thereby, the nozzle 59 communicates with the U-shaped conduit 61a. A U-shaped conduit 61b, which is connected to the liquid feed path 40, penetrates a front surface portion of the nozzle 59 on the opposite end wall 59b side (on the upper side in FIG. 15A) of the nozzle 59 and is open to the inside of the nozzle 59. Thereby, the nozzle 59 communicates with the U-shaped conduit 61b. Accordingly, the opening portions of the gas feed path 39 and the liquid feed path 40 are opposed to the distal end face of the distal end section body 36.

A confluent portion 61 is provided at an intermediate part of the nozzle 59. A jet outlet 53 is provided at a central position of the inner peripheral wall of the nozzle 59. The jet outlet 53 is disposed at a position facing the confluent portion 61. Thus, the jet outlet 53 is configured to jet the gas/liquid mixture fluid, which is made confluent and mixed in the confluent portion 61, toward the observation window 38. The jet outlet 53 and the observation window 38 are disposed in such a positional relationship that the center line O2 of the observation window 38 is biased by an eccentricity amount (S) to the opening end side of the liquid feed path 40, relative to the center line O1 of the jet outlet 53.

With the above-described structure, the following advantageous effects can be obtained. Specifically, the confluent portion 61 of the nozzle 59 is provided on the same plane as the observation window 38 that is provided on the distal end section body 36. The gas supplied from the air feed path 39 and the liquid supplied from the liquid feed path 40 are mixed in the confluent portion 61 into an atomized gas/liquid mixture fluid. The atomized gas/liquid mixture fluid is jetted from the jet outlet 53 toward the observation window 38. Thereby, the contamination adhering to the observation window 38 can be blown off and cleaned by the gas/liquid mixture fluid that is jetted from the jet outlet 53.

FIG. 16A and FIG. 16B show a ninth embodiment of the invention. The structural parts common to those in the third to eighth embodiments (see FIG. 6 to FIG. 15B) are denoted by like reference numerals, and a description thereof is omitted.

An inclined surface 62 is provided on one side portion of the distal end section body 36 of the endoscope 31. An inclined nozzle 63 is provided to be integral with the distal end section body 36 along the inclined surface 62. A space portion 64 is provided in the inclined nozzle 63 along the inclined surface 62. The gas feed path 39 and liquid feed path 40 are open to the space portion 64. Thus, the opening portions of the gas feed path 39 and liquid feed path 40 are opposed to the inner surface of the inclined nozzle 63.

Further, a confluent portion 65 is provided at a central position of the space portion 64 of the inclined nozzle 63. A jet outlet 66 is provided to be opposed to the confluent portion 65. Thus, the jet outlet 66 is configured to jet the gas/liquid mixture fluid, which is made confluent and mixed in the confluent portion 65, toward the observation window 38. The jet outlet 66 and the observation window 38 are disposed in such a positional relationship that the center line O2 of the observation window 38 is biased by an eccentricity amount (S) to the opening end side of the liquid feed path 40, relative to the center line O1 of the jet outlet 66.

With the above-described structure, the following advantageous effects can be obtained. Specifically, the confluent portion 65 of the inclined nozzle 63 is provided on the rear side of the observation window 38 that is provided on the distal end section body 36. The gas supplied from the air feed path 39 and the liquid supplied from the liquid feed path 40 are mixed in the confluent portion 65 into an atomized gas/liquid mixture fluid. The atomized gas/liquid mixture fluid is jetted from the jet outlet 66 toward the observation window 38. Thereby, the contamination adhering to the observation window 38 can be blown off and cleaned by the gas/liquid mixture fluid that is jetted from the jet outlet 66.

Figure 17A:
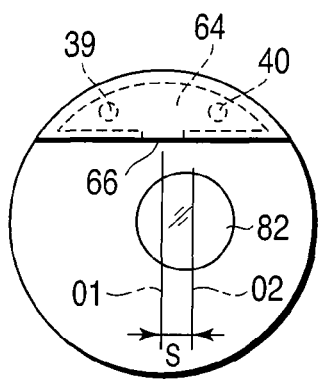
FIG. 17A is a front view of a distal end section body according to a tenth embodiment of the present invention.
Figure 17B:
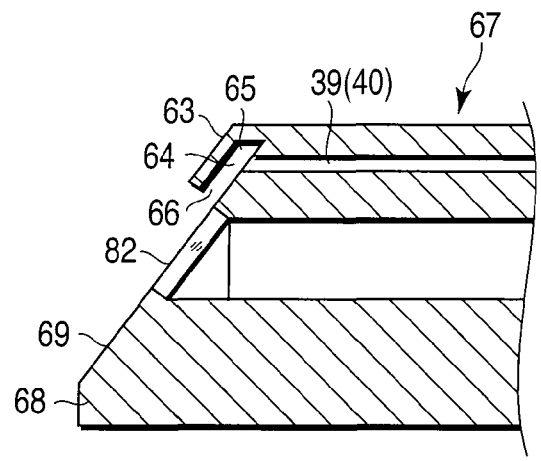
FIG. 17B is a longitudinal cross-sectional side view of the distal end section body.
Figure 18:
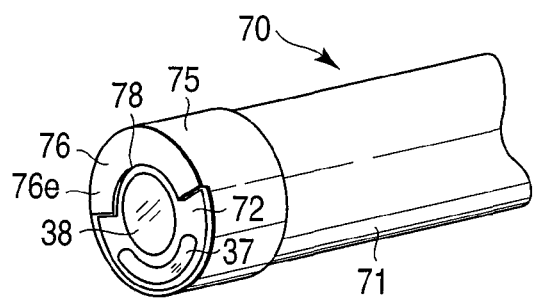
FIG. 18 is a perspective view of a distal end cap-equipped endoscope according to an eleventh embodiment of the invention.

FIG. 17A and FIG. 17B show a tenth embodiment of the invention. The structural parts common to those in the third to ninth embodiments (see FIG. 6 to FIG. 16B) are denoted by like reference numerals, and a description thereof is omitted.

The present embodiment is applied to an oblique-viewing endoscope 67. As shown in FIG. 17B, an inclined surface 69 is provided on a front end portion of a distal end section body 68 of the oblique-viewing endoscope 67. An observation window 82 is provided on the inclined surface 69. On one side portion of the inclined surface 69, an inclined nozzle 63 is provided to be integral with the distal end section body 68 along the inclined surface 69. The inclined nozzle 63 has basically the same structure as in the ninth embodiment (see FIG. 16A and FIG. 16B). A space portion 64 is provided along the inclined surface 69. The gas feed path 39 and liquid feed path 40 are open to the space portion 64. Thus, the opening portions of the gas feed path 39 and liquid feed path 40 are opposed to the inner surface of the inclined nozzle 63. Further, a confluent portion 65 is provided in the space portion 64 of the inclined nozzle 63. A jet outlet 66 is provided to be opposed to the confluent portion 65. Thus, the jet outlet 66 is configured to jet the gas/liquid mixture fluid, which is made confluent and mixed in the confluent portion 65, toward the observation window 82. In addition, the jet outlet 66 and the observation window 82 are disposed in such a positional relationship that the center line O2 of the observation window 82 is biased by an eccentricity amount (S) to the opening end side of the liquid feed path 40, relative to the center line O1 of the jet outlet 66.

With the above-described structure, the following advantageous effects can be obtained. Specifically, the confluent portion 65 of the inclined nozzle 63 is provided on the same plane as the observation window 82 that is provided on the distal end section body 68. Thereby, the gas supplied from the air feed path 39 and the liquid supplied from the liquid feed path 40 are mixed in the confluent portion 65 into an atomized gas/liquid mixture fluid. The atomized gas/liquid mixture fluid is jetted from the jet outlet 66 toward the observation window 82. Thereby, the contamination adhering to the observation window 82 can be blown off and cleaned by the gas/liquid mixture fluid that is jetted from the jet outlet 66.

In the third to tenth embodiments, the flexible endoscopes have been described. Needless to say, these embodiments are also applicable to rigid endoscopes.

FIG. 18 to FIG. 21 show an eleventh embodiment of the invention. The structural parts common to those in the third to tenth embodiments (see FIG. 6 to FIG. 17B) are denoted by like reference numerals, and a description thereof is omitted.

Figure 19:
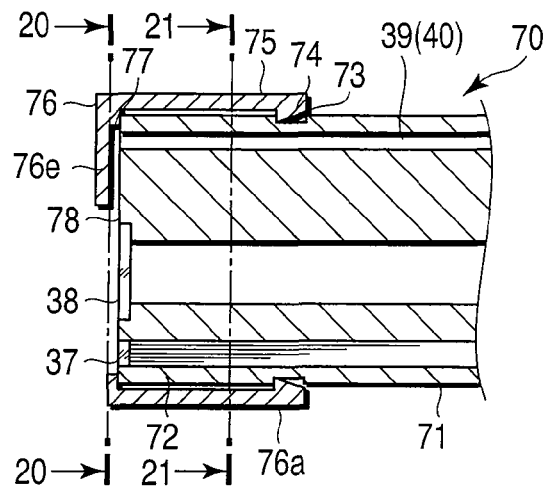
FIG. 19 is a longitudinal cross-sectional side view of a distal end section body of the distal end cap-equipped endoscope according to the eleventh embodiment.

The present embodiment shows a distal end cap-equipped endoscope. An observation window 38 and an illumination window 37 are provided on a distal end section body 72 of an insertion section 71 of a flexible endoscope 70. In addition, as shown in FIG. 19, a gas feed path 39 and a liquid feed path 40 are provided in the insertion section 71. Openings of the gas feed path 39 and liquid feed path 40 are provided on a front end face of the distal end section body 72.

Further, an annular engagement groove 73 is provided on an outer peripheral surface of the distal end section body 72. A distal end cap 75 is detachably attached to the distal end section body 72. The distal end cap 75 has an engagement projection 74 which is engaged with the engagement groove 73.

The distal end cap 75 is a circular cylindrical member. In the front end portion of the distal end cap 75, an arcuate nozzle 76 is integrally provided along the outer peripheral portion of the distal end cap 75. Specifically, the nozzle 76 includes a space portion 76f which is surrounded by an outer peripheral wall 76a extending along the outer peripheral portion of the distal end cap 75, an inner peripheral wall 76b surrounding a part of the outer periphery of the observation window 38, left and right end walls (left end wall 76c, right end wall 76d) in FIG. 20, and an arcuate front wall 76e. The space portion 76f is curved in an arcuate shape according to the curvature of the outer peripheral wall 76a and inner peripheral wall 76b. Further, the gas feed path 39 is open on the left end wall 76c side in the space portion 76f of the nozzle 76. On the opposite right end wall 76d side, the liquid feed path 40 is open. Accordingly, the gas feed path 39 and the liquid feed path 40 are open to the front end side of the distal end cap 75, and are opposed to the inner surface of the front wall 76e of the nozzle 76.

An intermediate part in the longitudinal direction of the nozzle 76 is provided with a confluent portion 77 which combines and mixes the gas that is supplied from the gas feed path 39 and the liquid that is supplied from the liquid feed path 40. Further, a jet outlet 78 is provided in the inner peripheral wall 76b of the nozzle 76, which is opposed to the confluent portion 77. The jet outlet 78 is configured to jet the gas/liquid mixture fluid, which is made confluent and mixed in the confluent portion 77, toward the observation window 38. In addition, the jet outlet 78 and the observation window 38 are disposed in such a positional relationship that the center line O2 of the observation window 38 is biased by an eccentricity amount (S) to the opening end side of the liquid feed path 40, relative to the center line O1 of the jet outlet 78.

With the above-described structure, the following advantageous effects can be obtained. Specifically, the confluent portion 77 of the nozzle 76 is provided on the same plane as the observation window 38 that is provided on the distal end section body 72. Thereby, the gas supplied from the air feed path 39 and the liquid supplied from the liquid feed path 40 are mixed in the confluent portion 77 into an atomized gas/liquid mixture fluid. The atomized gas/liquid mixture fluid is jetted from the jet outlet 78 toward the observation window 38. Thereby, the contamination adhering to the observation window 38 can be blown off and cleaned by the gas/liquid mixture fluid that is jetted from the jet outlet 78.

The present invention is not limited directly to the above-described embodiments. In practice, the structural elements can be modified and embodied without departing from the spirit of the invention. Various inventions can be made by properly combining the structural elements disclosed in the embodiments. For example, some structural elements may be omitted from all the structural elements disclosed in the embodiments. Furthermore, structural elements in different embodiments may properly be combined.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
    an insertion section which is configured to be inserted in a body cavity;
    a distal end section body comprising a distal end section of the insertion section and has at least an observation window at a flat surface of a distal end surface;
    a first flow path positioned and configured to communicate with a first fluid source so as to supply liquid and has an opening end open to a more outer peripheral side than the observation window on the flat surface of the distal end surface;
    a second flow path positioned and configured to communicate with a second fluid source so as to supply air and has an opening end open to a more outer peripheral side than the observation window on the flat surface of the distal end surface apart from the opening end of the first flow path; and
    a nozzle formed in an arcuate shape along an outer peripheral portion of the distal end surface to form a spatial communication between the first flow path and the second flow path so that the liquid supplied from the first flow path and the air supplied from the second flow path are mixed at an area above the arcuate shaped nozzle to yield a mixture fluid, the nozzle having a jet outlet configured to jet out the mixture fluid, passing across the observation window,
    wherein the jet outlet of the nozzle is disposed offset on the arcuate shaped nozzle formed by the first flow path and the second flow path, the offset from a center equally distant from the opening end of the first flow path and the opening end of the second flow path being closer to the opening end of the second flow path, and the jet outlet of the nozzle is formed in a linearly tapered shape such that an outer opening area of the jet outlet toward the observation window is smaller than an opening area at the spatial communication area.

2. The endoscope according to claim 1, wherein the jet outlet is disposed on a plane which is continuous with, or substantially parallel to, a plane in which the observation window is disposed.

3. A distal end cap-equipped endoscope comprising:
    an insertion section which is configured to be inserted in a body cavity;
    a distal end section body comprising a distal end section of the insertion section and has at least an observation window at a flat surface of a distal end surface;
    a first flow path positioned and configure to communicate with a first fluid source so as to supply liquid and has an opening end open to a more outer peripheral side than the observation window on the flat surface of the distal end surface;
    a second flow path positioned and configure to communicate with a second fluid source so as to supply air and has an opening end open to a more outer peripheral side than the observation window on the flat surface of the distal end surface apart from the opening end of the first flow path;
    a distal end cap which is detachably attached to the distal end section body, the distal end cap is structured as a nozzle formed in an arcuate shape along an outer peripheral portion of the flat surface of the distal end surface to form a spatial communication between the first flow path and the second flow path so that the liquid supplied from the first flow path and the air supplied from the second flow path are mixed at an area above the arcuate shaped nozzle to yield a mixture fluid, the nozzle having a jet outlet configured to jet out the mixture fluid, passing across the observation window;
    wherein the jet outlet of the nozzle is disposed offset on the arcuate shaped nozzle formed by the first flow path and the second flow path, the offset being closer to the opening end of the second flow path than the opening end of the first flow path in a direction orthogonal to a central axis running through a center of the distal end surface of the jet outlet.

4. The distal end cap-equipped endoscope according to claim 3, wherein the jet outlet is disposed on a plane which is continuous with, or substantially parallel to, a plane in which the observation window is disposed.

5. An endoscope cleaning sheath comprising:
    a cleaning sheath body which is fitted over an insertion section of an endoscope having at least an observation window at a flat surface of a distal end surface of a distal end section body;
    a first flow path positioned and configured to communicate with a first fluid source to supply liquid and has an opening end open to a more outer peripheral side than the observation window on the distal end surface;
    a second flow path positioned and configured to communicate with a second fluid source so as to supply air and has an opening end open to a more outer peripheral side than the observation window on the distal end surface apart from the opening end of the first flow path; and
    a nozzle which is formed in an arcuate shape along an outer peripheral portion of the distal end surface to form a spatial communication between the first flow path and the second flow path so that the liquid supplied from the first flow path and the air supplied from the second flow path are mixed at an area above the arcuate shaped nozzle to yield a mixture fluid, the nozzle having a jet outlet configured to jet out the a mixture fluid, passing across the observation window,
    wherein the jet outlet of the nozzle is disposed offset on the arcuate shaped nozzle formed by the first flow path and the second flow path, the offset being closer to the opening end of the second flow path than the opening end of the first flow path in a direction orthogonal to a central axis running through a center of the distal end surface of the jet outlet.

6. The endoscope cleaning sheath according to claim 5, wherein the jet outlet is disposed on a plane which is continuous with, or substantially parallel to, a plane in which the observation window is disposed.

* * * * *